United States Patent [19]
Heimreid

[11] Patent Number: 5,407,437
[45] Date of Patent: Apr. 18, 1995

[54] CLOSURE OF A MEDICAMENT WELL

[75] Inventor: Bent Heimreid, Junoveien 19, N-3942 Skjelsvik, Norway

[73] Assignees: Bent Heimreid, Skjelsvik; Otto T. Preiss, Oslo, both of Norway

[21] Appl. No.: 185,872

[22] PCT Filed: Jul. 23, 1991

[86] PCT No.: PCT/NO91/00103
§ 371 Date: Jan. 21, 1994
§ 102(e) Date: Jan. 21, 1994

[87] PCT Pub. No.: WO/9301848
PCT Pub. Date: Jul. 23, 1991

[51] Int. Cl.$^6$ .............................................. A61M 5/00
[52] U.S. Cl. .................................. 604/256; 604/124; 141/25
[58] Field of Search ............... 604/212, 217, 185, 256, 604/126, 122, 124, 45, 51, 251–252; 141/67, 25–28

[56] References Cited

U.S. PATENT DOCUMENTS

| | | | |
|---|---|---|---|
| 1,166,338 | 12/1915 | Duggan . | |
| 1,267,616 | 12/1916 | Abramovitz | 604/217 |
| 1,654,267 | 12/1927 | Mulford | 604/212 |
| 1,822,296 | 9/1930 | Keilly | 604/217 |
| 1,941,441 | 1/1933 | Miller | 604/217 |
| 2,195,281 | 10/1937 | Neuwirth | 604/217 |
| 2,514,576 | 2/1947 | Hein et al. | 604/212 |
| 2,635,603 | 6/1950 | Smith | 604/217 |
| 4,666,427 | 5/1987 | Larsson . | |

*Primary Examiner*—C. Fred Rosenbaum
*Assistant Examiner*—Perry E. Van Over
*Attorney, Agent, or Firm*—Cushman, Darby & Cushman

[57] ABSTRACT

A closure for a medicament well (1) with a central closing luer-shaped body (2) and, if desired, a round body (2), and a luer-lock skirt extending substantially in parallel with the latter, comprises a void (4), which is provided in the upper end of closure (2) and defined against the outside by a flexible wall (5) on the upper side and on the other side is made to communicate with the outside, via a channel (6) extending through body (2).

1 Claim, 3 Drawing Sheets

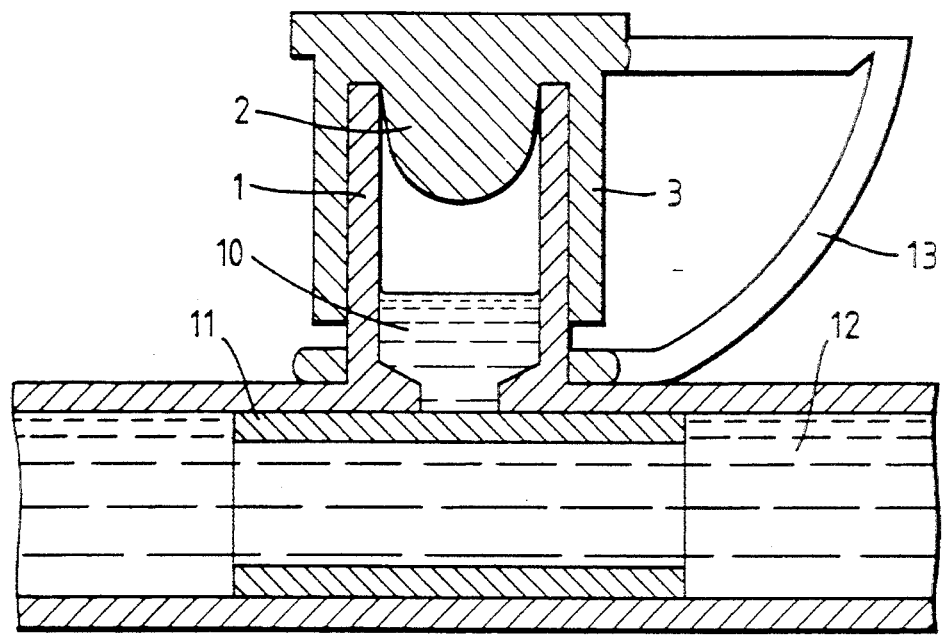
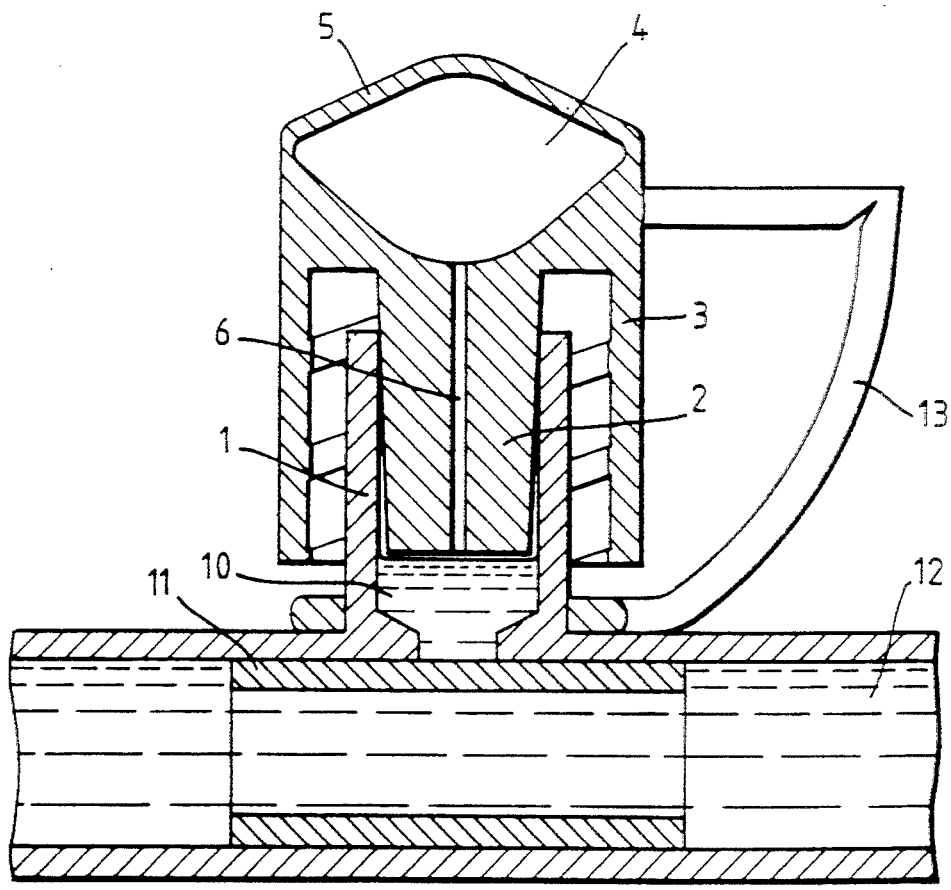

CLOSURE OF A MEDICAMENT WELL

BACKGROUND OF THE INVENTION

The present invention relates to a closure for a medicament well.

More precisely, the invention relates to a closure for a medicament well on a cannula, with a central, closing body and, if desired, a round body and a skirt extending substantially in parallel with the latter.

There is mainly one kind of intravenous cannulae on the market at present, viz. a kind where a circular medicament well projecting normally to the liquid channel in the intravenous cannula is closed from above by the aid of a conventional cap, which is commonly fastened to the sleeve of the medicament well by the aid of a more or less sturdy fastening strap.

The present cannulae with a medicament well of a conventional kind show the inherent deficiency that after administration of medicament and removal of the administrating syringe, there is always a small volume of medicament solution left in the well due to the counterpressure from the liquid flowing in the cannula.

This phenomenon may represent quite a health hazard, since the volume of medicament remaining in the medicament well may act as a substrate for bacteria, or the medicament may be subjected to decomposition or metamorphosis due to influence from the outside environment.

This is probably one of the reasons for the fact that this kind of intravenous cannula is not accepted by the FDA on the American market.

Body heat may also cause undesirable changes.

Often, hours may pass between each time the medicament well is used, and this enhances the hazard of undesirable changes.

When the medicament well is used again, the medicament phase which may be modified or decomposed will be pushed into the cannula and introduced into the body, which may cause undesirable and even dangerous states.

Another aspect that should be considered in this connection is that when small volumes of medicaments are administered it may occur that not all of the medicsment is injected, since some of it is left in the well.

SUMMARY OF THE INVENTION

It is an object of the present invention to remedy the shortcomings of known technology and to provide a device which permits complete discharge of the well. In this manner, any hazard of administrating contaminated material to the patient is avoided, decomposition or modification of a medicament remaining in the well is avoided, and complete administration of the medicament to the patient is ensured.

This is achieved by the aid of a closure of the above mentioned kind, and this closure is characterized by a void provided in the upper end of the closure, which is defined against the outside on top by a flexible wall and is on the other side made to communicate with the outside, via s channel extending through the closure body.

BRIEF DESCRIPTION OF THE DRAWINGS

The invention is disclosed in more detail with reference to the accompanying drawings, in which:

FIG. 2 shows a conventional closure;

FIG. 3 shows a closure according to the invention in the same phase as the conventional closure according to FIG. 2.

DETAILED DESCRIPTION

Figure 1:
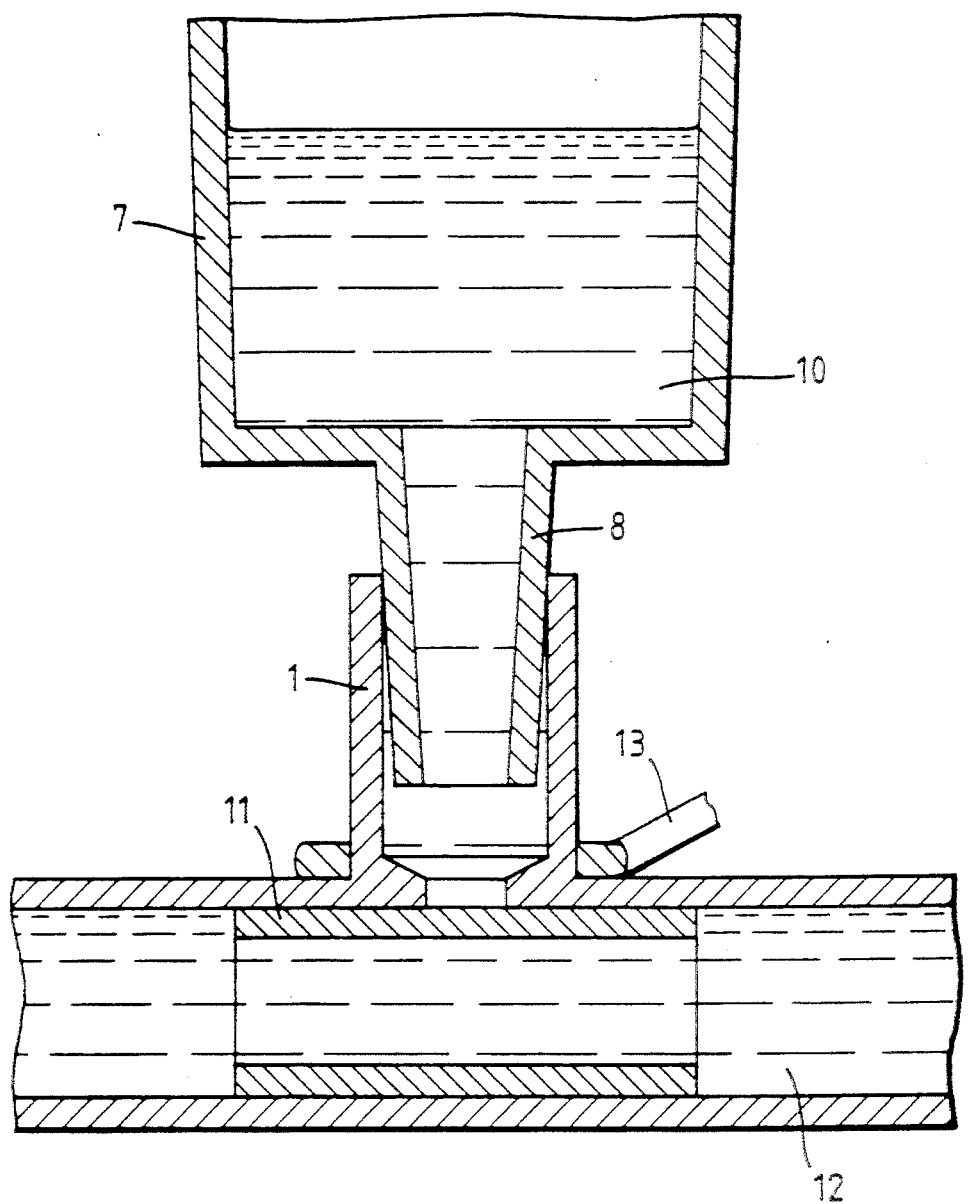
FIG. 1 shows a medicament well with an inserted syringe for administration of a medicament.

In FIG. 1, the luer 8 of a syringe 7 is inserted into the medicament well 9 1 of a cannula, for administration of medicament solution 10.

Figure 4:
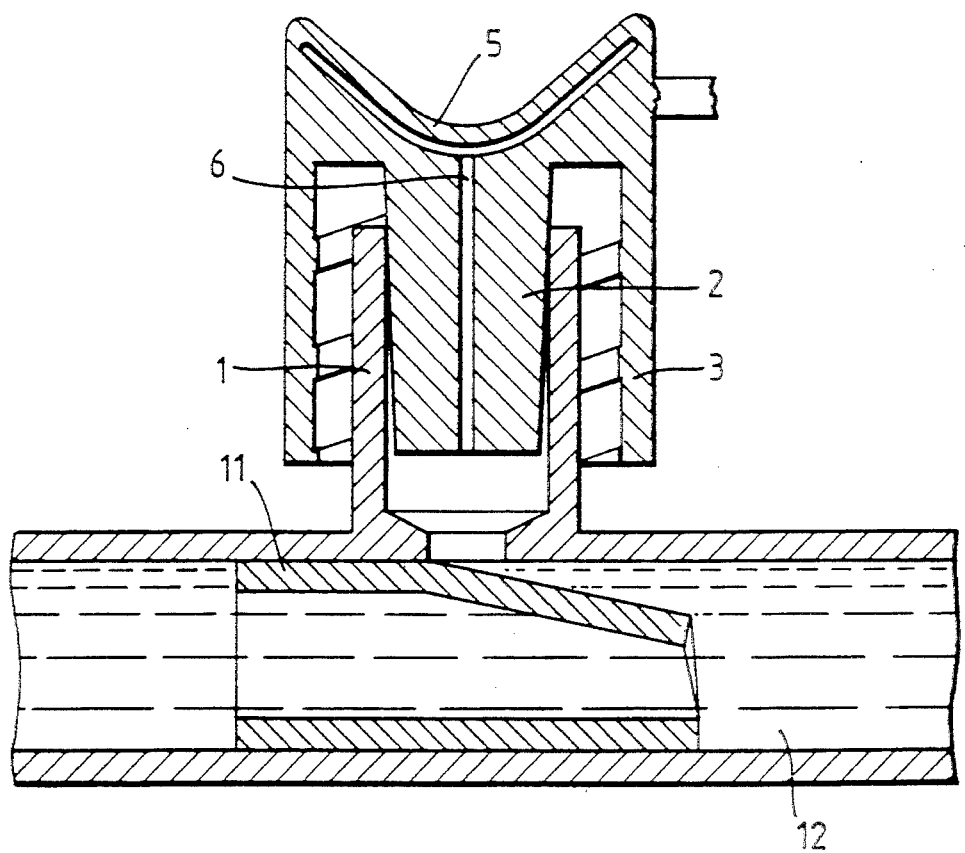
FIG. 4 shows a closure according to the invention immediately after the remaining residue was squeezed out of the well.

When medicanent solution 10 is injected into the liquid path 12 inside the cannula, a flexible tubular valve 11 is urged to temporarily open, as indicated in FIG. 4. Upon completed injection the counter-pressure in liquid 12 urges valve 11 back into contact with the cannula sidewall, including about the perimeter of the juncture 15 of the well with the cannular sidewall, thereby closing of the well from the liquid path inside the cannular, at that juncture. Upon removal of syringe 10 and insertion of a closure the situation is as shown in FIG. 2 and 3, with a conventional closure, 2, 3, 13 and a closure 2, 3, 4, 5, 6, 13, according to the invention, respectively.

A residue of medicament solution 10 will remain on the bottom of well 1, in both the conventional device (FIGS. 1 and 2) and the device according to the present invention (FIGS. 1 and 3). This residue may, as mentioned above, be subjected to decomposition of metamorphosis, and/or it may represent great values of economic and therapeutic kinds.

Use of the closure, according to the invention, permits utilization of the residue 10 as well by removing the residue 10 from the well 1 and urging it into the liquid path 12.

This is achieved by the aid of the arrangement according to the invention by the fact that the flexible wall 5 which defines an air-filled void 4 uppermost in the closure is compressed, as shown in FIG. 4. Consequently, air is discharged from within the enclosed void 4 through the channel 6 in the central body 2 of the closure, into the location of the residual liquid 10 and urges residual liquid 10 past the valve 11 and into the liquid path 12.

Upon compression the domed flexible wall 5 which overlies the void 4, towards the dished depression or seat 14 which underlies the void 4, such as to materially diminish the volume of the of void 4 and resultant displacement of the residual liquid 10 through the juncture 15, and past the valve 11 into the liquid path 12 within the cannula 9, the counterpressure in the liquid 12 causes the valve 11 to again contact the cannula wall 1 perimetrically of the juncture 15 and circumferentially of the sidewall of the cannula 9, thereby again closing off the well 1 from the liquid path 12.

The channel 6 formed within the externally tapered central body or plug 2 of the closure extends axially between the center of the dished seat 14 and the axially inner end 16 of the body 2, in the portion of the space enclosed by the well 1, axially between the body 2 and the juncture 15, where the residue 10 is located during the FIG. 3 state.

The invention is preferably used for closures of respective cannulae wells which are fastened to the cannula, e.g. each by the aid of a respective strap 13. However, there is nothing to prevent the closure according to the invention from being separate and used on various kinds of multi-way valves and cocks, as commonly used within this field of medical technology, so as to solve the same problems as regards residues of medicaments.

According to an especially preferred feature of the invention, the difference in volume of the void 4 between the expanded (FIG. 3) and compressed (FIG. 4) states thereof is substantially equal to the volume of the residue of medicament solution 10 remaining at the bottom of well 1 in the FIG. 3 state for complete removal of the residue without air being introduced into the liquid flow 12.

It is, thus, possible to remove remaining medicament solution from wells or corresponding injection sleeves in a simple and hygienic manner in order to avoid the above-indicated problems in a simple and safe manner.

I claim:

1. A closure for closing, and flushing liquid residue from an outwardly opening, peripherally walled medicament well which at a base thereof has a juncture through an opening normally closed by a backflow-preventing check-valve, with a liquid path extending generally at a right angle to the well, centrally of the tubular sidewall of cannula, said closure comprising:

a plug having an axially inner end, and axially outer end and a sidewall sized to permit the plug to be telescoped into the well to a given axial extent limited by engagement of a feature on the plug with a feature on the cannula, at which the plug sealingly closes the well distally of the base of the well and leaves a medicament residue-accommodating chamber having a first given volume within the well between the axially inner end of the plug and the juncture of the base of the well;

the outer end of said plug including an outwardly dished depression covered by a flexible dome wall which in a first state thereof is outwardly bulged and which is perimetrically joined to said plug so as to overlay said dished depression and form therewith in said first state thereof an enclosed, normally air-filled void having a second given volume, and which flexible dome wall in a second state thereof is internally convex towards said depression and thereby substantially diminish said void volumetrically to a third given volume;

a passageway defined axially through said plug from said and through depression to and through said inner end of said plug;

the difference between said second and third given volumes being substantially equivalent to the portion of said first given volume which in normal expected use of said cannula is occupied by residual medicament liquid upon conclusion of an incident of dispensing of medicament liquid through said well into said liquid path.

* * * * *